United States Patent
Yu et al.

(10) Patent No.: US 8,686,053 B2
(45) Date of Patent: Apr. 1, 2014

(54) ALGINIC ACID WITH LOW MOLECULAR WEIGHT, ITS SALTS, USES, PREPARATIVE METHODS, PHARMACEUTICAL COMPOSITIONS AND FOODS

(75) Inventors: Chuanxing Yu, Dalian (CN); Deshan Li, Dalian (CN)

(73) Assignee: Chuanxing Yu, Dalian (CN)

( * ) Notice: Subject to any disclaimer, the term of this patent is extended or adjusted under 35 U.S.C. 154(b) by 662 days.

(21) Appl. No.: 12/816,396

(22) Filed: Jun. 16, 2010

(65) Prior Publication Data

US 2010/0256090 A1  Oct. 7, 2010

Related U.S. Application Data

(63) Continuation-in-part of application No. PCT/CN2007/071404, filed on Dec. 29, 2007.

(51) Int. Cl.
*D21H 19/02* (2006.01)

(52) U.S. Cl.
USPC .............................................. 514/779; 536/3

(58) Field of Classification Search
USPC .............................................. 536/3; 514/779
See application file for complete search history.

(56) References Cited

U.S. PATENT DOCUMENTS

2010/0069323 A1*  3/2010  Seto et al. ................... 514/54

FOREIGN PATENT DOCUMENTS

| CN | 1156150 A | 8/1997 |
|---|---|---|
| CN | 1445365 A | 10/2003 |
| CN | 1157415 C | 7/2004 |
| CN | 1513998 A | 7/2004 |
| CN | 1562071 A | 1/2005 |
| CN | 1920003 A | 2/2007 |
| CN | 101074246 A | 11/2007 |
| WO | WO 0140315 A1 * | 6/2001 |

OTHER PUBLICATIONS

PCT International Search Report for Int'l Application No. PCT/CN2007/071404, Filed Dec. 29, 2007, Dated Oct. 16, 2008.
PCT Written Opinion for Int'l Application No. PCT/CN2007/071404, Filed Dec. 29, 2007, Dated Oct. 16, 2008.
PCT International Preliminary Report on Patentability for Int'l Application No. PCT/CN2007/071404, Filed Dec. 29, 2007, Dated Mar. 24, 2010.
First Office Action issued by the State Intellectual Property Office China to Chinese counterpart application CN200780101830.1., dated Jul. 26, 2011.

* cited by examiner

*Primary Examiner* — Patrick Lewis
*Assistant Examiner* — Everett White
(74) *Attorney, Agent, or Firm* — US-China Intellectual Property Counsel, PLLC

(57) ABSTRACT

The present invention discloses an alginic acid and/or its salts with low molecular weight, wherein the weight average molecular weight of the alginic acid is from about 700 to about 4500 Daltons, and the molar ratio of guluronic acid to mannuronic acid in the alginic acid is from about 0.6 to about 19. The present invention also discloses the preparative method of making the alginic acid and/or its salts thereof, and the use of them for treating hypertension, chronic renal failure and postprandial hyperglycemia induced by glycosidase. The present invention further discloses pharmaceutical compositions and foods containing the alginic acid with low molecular weight and/or salts thereof as active component.

21 Claims, No Drawings

ALGINIC ACID WITH LOW MOLECULAR WEIGHT, ITS SALTS, USES, PREPARATIVE METHODS, PHARMACEUTICAL COMPOSITIONS AND FOODS

CROSS REFERENCES

This application is a continuation-in-part application of PCT Application Serial No. PCT/CN2007/071404 filed on Dec. 29, 2007. The entire disclosures of the preceding applications are incorporated by reference herein in their entirety.

FIELD OF INVENTION

The present invention relates to an alginic acid with low molecular weight and its salts, their uses and preparative methods, the pharmaceutical compositions and the health foods containing the same.

BACKGROUND

Alginic acid is a polysaccharide. Alginic acid is generally comprised of mannuronic acid units (hereinafter referred to as "M") and guluronic acid units (hereinafter referred to as "M"), which are randomly linked as linear long-chain molecules. Natural alginic acid (such as brown algae) has a G to M molar ratio of 0.2 to 2.5 and a molecular weight of 100,000 to 1,500,000 Da.

Alginic acid is usually used for products such food, medicine, textile, printing and dyeing, paper making, daily chemical and the like as a thickening agent, emulsifier, stabilizer, adhesive, sizing agent, etc. Researches have already shown that degradation of alginic acid will generate an alginic acid having low molecular weight, for example, from 5,000 Da to 20,000 Da in average with pharmacological activity.

For example, CN 1157415C has disclosed salts of alginic acid with low molecular, which have an average molecular weight of 5,000 to 20,000 Da, while most of which have a molecular weight of 1,000 to 30,000 Da, and a Ubbelohde intrinsic viscosity number between 3 and 20, wherein the salt-forming ions of the said alginate are pharmaceutically acceptable cations. The said salts of alginic acid with low molecular have a certain effect on reducing blood pressure and blood glucose.

However, the activity of alginic acid or its salts with lower molecular weight in reducing blood pressure and blood glucose still needs to be proved, and research and development still need to be made to find whether they have other pharmacological actions. Moreover, due to variations in sources of raw material and preparation conditions, it is difficult to ensure different batches of the prepared alginic acid with low molecular weight or its salts to have excellent uniformity.

SUMMARY OF INVENTION

One object of the present invention is to provide a novel alginic acid with low molecular weight and its salts, their uses, preparative methods, the pharmaceutical compositions and the health foods comprising the same as active ingredients.

The present invention provides an alginic acid with low molecular weight, which has a weight average molecular weight ranges from about 700 to about 4,500 Da, and the molar ratio of the guluronic acid units to mannuronic acid units in said alginic acid ranges from about 0.6 to about 19.

The present invention provides a salt of alginic acid with low molecular weight, wherein said salt of alginic acid with low molecular weight is the salt of the alginic acid with low molecular weight according to the present invention.

The present invention further provides uses of said alginic acid with low molecular weight and/or its salts for the manufacturing of medicaments for the treatment of hypertension, chronic renal failure and postprandial hyperglycemia caused by glycosidase The present invention further provides a method for preparing said alginic acid with low molecular weight, comprising degrading an alginic acid raw material, which has a weight average molecular weight of about 10,000 to about 1,500,000 Da and has a G to M molar ratio no less than about 0.3 in an acid environment having a hydrogen ion concentration ranging from about 0.3 to about 0.5 mol/L at a temperature ranging from about 80 to about 100° C. under a pressure ranging from about 0.08 to about 0.13 Mpa for about 0.5 to about 8 hours.

The present invention further provides a method for preparing said salt of alginic acid with low molecular weight, comprising preparing an alginic acid with low molecular weight with the method as described above, then treating the resultant alginic acid with alkaline substance to prepare a salt of alginate acid with low molecular weight.

The present invention further provides a pharmaceutical composition for treating hypertension, wherein said composition comprises an alginic acid with low molecular weight and/or the salt of alginic acid with low molecular weight and a pharmaceutically acceptable carrier; Said alginic acid with low molecular weight is selected from the alginic acid with low molecular weight according to the present invention; Said salt of the alginic acid with low molecular weight is selected from the salt of the alginic acid with low molecular weight according to the present invention.

The present invention further provides a pharmaceutical composition for treating chronic renal failure, wherein the said composition comprises an alginic acid with low molecular weight and a pharmaceutically acceptable carrier, wherein the alginic acid with low molecular weight is selected from the alginic acid with low molecular weight according to the present invention.

The present invention further provides a pharmaceutical composition for treating postprandial hyperglycemia caused by glycosidase, wherein the said composition comprises an alginic acid with low molecular weight and/or the salt of alginic acid with low molecular weight and a pharmaceutically acceptable carrier, wherein said alginic acid with low molecular weight is selected from the alginic acid with low molecular weight according to the present invention and the salt of the alginic acid with low molecular weight is selected from the salts of the alginic acid with low molecular weight according to the present invention The present invention further provides a health food comprising an alginic acid with low molecular weight and/or a salt of alginic acid with low molecular weight according to the present invention.

The alginic acid with low molecular weight and/or its salts provided by the present invention have excellent effect on treating hypertension, chronic renal failure and postprandial hyperglycemia caused by glycosidase, and can be used in the preparation of pharmaceutical compositions for treating said diseases, and can also be added into foods in an proper amount to prevent and relieve said diseases. Moreover, an alginic acid with low molecular weight and its salts with high uniformity can be prepared using different brown algae raw materials (such as those raw materials which have weight-average molecular weight of about 10,000 to about 1,500,000 Da and whose molar ratio of guluronic acid units to mannuronic acid units is no less than about 0.3 according to the preparative method provided by the present invention.

DETAIL DESCRIPTION OF INVENTION

The alginic acid with low molecular weight provided by the present invention has a weight-average molecular weight ranging from about 700 to about 4,500 Da and a G to M molar ratio of about 0.6 to about 19. It is hard for an alginic acid with low molecular weight to be absorbed via digestive tract if the molecular weight thereof is too high, hardly can it be used in injection since its solubility is poor, either; whereas it tends to break down into to monosaccharides (such as guluronic acid and mannuronic acid) as long as the molecular weight of the alginic acid with low molecular weight is too low, thus results in losing the pharmacological activity of the polysaccharide chain thereof.

The weight-average molecular weight and G to M molar ratio of the degradation product of an alginic acid, i.e., the alginic acid with low molecular weight, can be measured by conventional methods employed in the art, for example, by reacting an alginic acid with low molecular weight product from the degradation of an alginic acid with alkaline substance (such as sodium hydroxide) and it gives a soluble salt of the alginic acid with low molecular weight, and then using the mini DAWN TREOS laser light scattering instrument from American Wyatt Company (WTC), and 150c, PL220c and ALLIANCE 2000 from American Waters Company in combination according to their instructions to determine the molecular weight and molecular weight distribution of the alginic acid with low molecular weight, and to calculate the weight-average molecular weight thereof.

Preferably, the weight average molecular weight of the alginic acid is about 1,000 Da to about 4,500 Da and the molar ratio of G to M ranges from about 1 to about 16; more preferably, the weight average molecular weight of said alginic acid ranges from about 2,500 Da to about 4,500 Da and the molar ratio of G to M ranges from about 1 to about 10, based on pharmacological action of alginic acid and/or its salts in the treatment of hypertension, chronic renal failure and postprandial hyperglycemia caused by glycosidase.

Preferably, the salts of the alginic acid with low molecular weight in the present invention may be selected from salts formed from said alginic acid with low molecular weight and a pharmaceutically acceptable cation(s). More preferably, said salt of the alginic acid with low molecular weight is selected from one or more of sodium salt, potassium salt, ammonium salt, calcium salt, magnesium salt and zinc salt of said alginic acid with low molecular weight. Most preferably, the salt of said alginic acid with low molecular weight is selected from sodium salt and/or potassium salt of said alginic acid with low molecular weight.

The present invention provides use of said alginic acid with low molecular weight and/or the salt of the alginic acid with low molecular weight for the manufacturing of medicaments for the treatment of hypertension, chronic renal failure and postprandial hyperglycemia caused by glycosidase.

The inventor discovered that, the alginic acid with low molecular weight and/or its salts of the present invention not only has prominent activity in treating hypertension and postprandial hyperglycemia caused by glycosidase, but also can reduce the symptoms of chronic renal failure patients. When used for the manufacturing of medicaments for treating hypertension and postprandial hyperglycemia caused by glycosidase, the alginate salts of the present invention are preferred for their excellent dispersibility in water. More preferably, the salts of said alginic acid with low molecular weight are potassium salt or sodium salt of said alginic acid with low molecular weight. When used for the manufacturing of medicaments for treating chronic renal failure, the alginic acid with low molecular weight of the present invention is preferred, considering that a chronic renal failure patient always suffers from metal ion metabolic disorder. More preferably, the alginic acid with low molecular weight used for a chronic renal failure patient has a weight average molecular weight ranging from about 2,500 to about 4,500 Da and a G to M molar ratio of about 0.6 to about 19.

Preferably, the method for preparing said alginic acid with low molecular weight provided in the invention comprises degrading an alginic acid raw material, which has a weight average molecular weight of about 10,000 to about 1,500,000 Da and has a G to M molar ratio no less than about 0.3, in an acid environment with a hydrogen ion concentration ranging from about 0.3 to about 0.5 mol/L at a temperature ranging from about 80 to about 100° C. under a pressure ranging from about 0.08 to about 0.13 Mpa for about 0.5 to about 8 hours. If the hydrogen ion concentration of the acid environment, the temperature, the pressure and the degradation time exceed too much than the foresaid upper limits, the alginic acid raw material will be excessively degraded, thus results in losing the pharmacology activity of polysaccharide chains of the alginic acid with low molecular weight; contrarily, if the hydrogen ion concentration of the acid environment, the temperature, the pressure and the degradation time is lower than the foresaid lower limits by too much, the alginic acid raw material will not be degraded to the expected level of the alginic acid with low molecular weight of the invention.

Raw material for preparing alginic acid is usually brown algae, and various brown algae such as kelp (e.g. *laminaria japonica*), *ectocarpus, Scytosiphon lomentarius, Pelvetia siliquosa, sargassum*, etc can be used. For consideration of cost, the raw material is preferably selected from one or more of kelp, kombu, *Pelvetia siliquosa, Sargassum fusiforme, Sargassum thunbergii, Sphacelaria Bipinnata, macrocystis* and *sargassum* (such as *Sargassum hemiphylluen, Sargassum Linifolium*). Due to the facts that alginic acid raw materials are from various sources and that the alginic acid content also varies from one another in different parts of same alginic acid raw material, plus various preparation conditions, it is difficult to ensure different batches of prepared alginic acid with low molecular weight or its salts to have excellent uniformity.

The inventor discovered that the alginic acid with low molecular weight of the present invention can be prepared by the degradation of alginic acid raw material, which has a weight average molecular weight of about 10,000 to about 1,500,000 Da and has a G to M molar ratio no less than about 0.3, in an acid environment with a hydrogen ion concentration ranging from about 0.3 to about 0.5 mol/L at a temperature ranging from about 80 to about 100° C. under a pressure ranging from about 0.08 to about 0.13 Mpa for about 0.5 to about 8 hours. The resultant alginic acid has a weight average molecular weight ranging from about 700 to about 4,500 Da and a G to M molar ratio of about 0.6 to about 19. Preferably, the alginic acid with low molecular weight of the present invention can be prepared by the degradation of a raw material, which has a weight average molecular weight of about 100,000 to about 300,000 Da and has a G to M molar ratio of about 0.5 to about 0.65, in an acid environment with a hydrogen ion concentration ranging from about 0.35 to about 0.45 mol/L at a temperature ranging from about 85 to about 95° C. under a pressure ranging from about 0.10 to about 0.12 Mpa for about 3 to about 5 hours. Given the alginic acid raw materials have same weight average molecular weight, the alginic acid with low molecular weight prepared by the method of the present invention contains higher guluronic acid, and the G to M molar ratio is up to about 0.6 to about 19, more preferably about 1 to about 16, and even more preferably, up to about 2 to about 16. The acid environment can be achieved by conventional methods employed in the art, for example, by addition of dilute hydrochloric acid and the like. In addition, the alginic acid raw material can also be selected from semi-products satisfying above conditions, such as alginic acid products manufactured by Qingdao Bright Moon Seaweed Groups Co. Ltd or Qingdao Nanyang Seaweed Industry Group Co. Ltd, etc, which have a weight average molecular weight between about 100,000 and about 300,000 Da and a G to M molar ratio of about 0.5 to about 0.65.

Preferably, the method for preparing the foresaid alginic acid with low molecular weight provided in the present invention also comprises one or more conventional degradation steps. For example, in one preferred embodiment, the method comprises a step of degrading a raw material, which has a weight average molecular weight of about 10,000 Da to about 1,500,000 Da and has a G to M molar ratio no less than about 0.3, in an acid environment having a hydrogen ion concentration ranging from about 0.3 to about 0.5 mol/L at a temperature ranging from about 85 to about 95° C. under a pressure ranging from about 0.11 to about 0.13 Mpa for about 0.5 to about 1 hour. Before and/or after the foregoing step, the method further comprises one or more conventional degradation steps selected from physical degradation step, photochemical degradation step, immobilized enzyme degradation step, chemical degradation step, or combinations thereof. The conventional degradation step(s) are preferably conducted before the foregoing step. The physical degradation step, photochemical degradation step, immobilized enzyme degradation step and oxidative degradation step are commonly known in the art and have already been disclosed in PCT/CN99/00202 and herein are entirely incorporated for reference. For example, physical degradation degradation step comprises ultrasonic process or high speed shearing process; photochemical degradation step utilizes optical radiation and catalysis; oxidative degradation step utilizes organic and inorganic oxidants, such as hydrogen peroxide, peracetic acid, potassium peroxide, potassium carbonateperoxide, potassium (sodium) perborate, potassium permanganate, ammonium persulfate, potassium hydrogen persulfate, potassium chlorite, sodium chlorite and etc; immobilized enzyme degradation step comprises immobilizing alginic acid lyase using porous sodium glass beads and then loading the beads in column for decomposition. It is preferable to initially degrade the alginic acid raw material to such extent that the raw material has a weight-average molecular weight of about 10,000 to about 30,000 Da using one or more steps of physical degradation step, photochemical degradation step, immobilized enzyme degradation step and oxidative degradation step, then conduct further degradation in an acid environment having a hydrogen ion concentration ranging from about 0.3 to about 0.5 mol/L at a temperature ranging from about 85 to about 95° C. under a pressure ranging from about 0.11 to about 0.13 Mpa for about 0.5 to about 1 hour.

The present invention also provides a method for preparing the salts of said alginic acid with low molecular weight; the method comprises preparing an alginic acid with low molecular weight by the method described above and then treating the same with an alkaline substance. The alkaline substance can be a hydroxide or its aqueous solution, which is capable of increasing pH value and whose cation is pharmaceutically acceptable, for example, it can be a sodium ion solution, a potassium ion solution, ammonia water, etc. Additionally, said salts may not contain a carboxyl group and can be derived from an inorganic base (e.g., sodium hydroxide, potassium hydroxide, ammonium hydroxide, calcium hydroxide or ferric hydroxide).

The alginic acid with low molecular weight and/or its salt of the present invention can be prepared together with the commonly known pharmaceutically acceptable carrier(s) into the pharmaceutical composition of the present invention. For example, they can be prepared into as a liquid composition, one example of liquid carriers is an asepsis liquor that does not contain any other material or active ingredient, such as an injection level water, or a pyrogen-free aqueous solution containing a buffer, such as the aqueous solution of sodium phosphate or physiological saline that has physiological pH, or both of them. Other liquid carriers may contain more than one buffer salts, such as sodium chloride, potassium chloride, glucose, propanediol, polyethyleneglycol, etc. However, the liquid composition of the pharmaceutical composition may also comprise a water-free liquid phase, such as glycerin, plant oil, organic ester or water-oil emulsion. Based on the total weight of the pharmaceutical composition, the pharmaceutical composition usually comprises at least 1 wt % of the alginic acid with low molecular weight and/or its salts according to the present invention.

To obtain expected preventing or treating effect, the dosage of administration or dose range of the pharmaceutical composition of the present invention usually varies depending on patients' age, physique, sex, also, the degree of disease. The dose for an individual is determined based on his basic disease(s) and other appeared symptoms. The precise dosage can be determined by a skilled person via commonly known ways and methods, for example, it can be determined based on variation of disease indexes (such as blood pressure, blood glucose, and so on) that are used as dosage function, or as a function of administration approach or drug carrier. The dose can be separately determined for an individual. For example, the dose exactly tolerated to a patient may be in a range of about 0.1-about 10000 μg/L (or μg/kg), more preferably, about 1-about 100 μg/L (or μg/kg), in blood plasma or in a particular organ. In addition, the dosage can be calculated based on body weight of the patient; in this case, the normal dosage of the pharmaceutical composition of the present invention must be regulated within the following ranges, such as about 0.1-about 1000 mg/kg, preferably, about 1-about 500 mg/kg of the body weight, and more preferably, about 1-about 50 mg/kg of the weight. Also, the dosage can be calculated based on a particular organ other than entirety of the patient, such situations comprise, for example, placing an implant, i.e., a biological polymer into which the alginic acid with low molecular weight and/or its salt of the present invention has been enclosed, close to the particular organ by surgery, whereby the pharmaceutical composition of the present invention can be administrated in solid state, gel state or liquid state.

The pharmaceutically acceptable carrier may also be selected from filler, diluent, adhesive, humectant, disintegrant, dissolution blocker, absorbefacient, wetting agent, absorbent and/or lubricant.

The filler and diluent are preferably selected from starch, lactose, sucrose, glucose, mannitol and silica dioxide; the adhesive is preferably selected from carboxymethylcellulose, alginate salt, gelatin and polyvinylpyrrolidone; the humectant is preferably selected from glycerol; the disintegrant is preferably selected from agar, calcium carbonate and sodium carbonate; the dissolution blocker is preferably selected from paraffin; the absorbefacient is preferably selected from quaternary ammonium compound; the wetting agent is preferably selected from cetanol and glycerin monostearate; the absorbent is preferably selected from kaolin and bentonite; the lubricant is preferably selected from talc, calcium stearate, magnesium stearate, solid polyethylene glycol, or mixture thereof.

The alginic acid with low molecular weight and/or its salt of the present invention can also be used as gel, medicinal powder, powder, tablet, retarder, premix, emulsion, liquid formulation, drop, concentrated solution, granule, syrup, pilule, bolus, capsule, gasoloid, spray and/or inhalant. The tablet, sugar-coated tablet, capsule, pill and granule can have a conventional coating, optionally have a casing comprising an opacifying agent, and have the following compositions, whereby the release of effective substances is performed in a delayed manner or only preferably performed at a proper location in the intestinal canal, wherein a terminated polymer and paraffine can be used as an encapsulating substance. The capsule is preferably an enteric capsule or a colon-soluble capsule. The material of said enteric capsule can be one or more selected from methacrylic acid/methyl acrylate copolymer, methacrylic acid/methyl methacrylate copolymer, methacrylic acid/ethyl acrylate copolymer and methacrylic acid/ethyl methacrylate copolymer; the two monomers of the foregoing copolymers usually have a molar ratio of 1:1 and the copolymers with this molar ratio are not soluble in acid solution (such as gastric juice) and are soluble in digestive juice (dissolved at small intestine) having a pH value greater than about 5.5, for example, the methacrylic acid/ethyl acrylate (1:1) copolymer is not soluble under pH value lower than about 5.5 and the methacrylic acid/ethyl methacrylate (1:1) copolymer is not soluble under pH value lower than about 6.0. The material of the colon-soluble capsule can be methacrylic acid/acrylate copolymer and/or methacrylic acid/methacrylate copolymer, the two monomers of the foregoing copolymer usually have a molar ratio of 1:2, and the copolymers with this molar ratio are not soluble in acid solution and neutral solution (such as gastric juice, digestive juice in the small intestine) and are soluble in body fluid (dissolved at colon) having a pH value greater than about 7.0, for example, the methacrylic acid/methyl methacrylate (1:2) copolymer is not soluble under pH value lower than about 7.0.

For example, the medicaments of the present invention can be orally administered in any orally allowable formulation, including, but not limited to, capsule, tablet, water-containing suspension and solution. In the case that the medicament is orally administrated in form of tablet, the commonly used carrier comprises lactose and cornstarch, in addition, a lubricant such as magnesium stearate is usually added. In the case that the medicament is orally administrated in form of capsule, the appropriate dilute comprises lactose and dry cornstarch. In the case that the medicament is orally administrated in form of water-containing suspension, the alginic acid with low molecular weight and/or its salts of the present invention are used with an emulsifier and a suspending agent in combination. Also, particular sweetener and/or flavouring agent and/or colorant, if needed, can be added.

The alginic acid with low molecular weight and/or its salts of the present invention can be optionally prepared into a microcapsule together with one or more of the above described carrier substances.

When the pharmaceutical composition of the present invention is a suppository, it may also comprise, besides the alginic acid with low molecular weight and/or its salts of the present invention, conventional water-soluble or water-insoluble carrier substance, such as polyethylene glycol, fat such as cocoa butter and higher ester (such as the ester of $C_{14}$ alcohol and $C_{16}$ fatty acid), or the mixture thereof.

When the pharmaceutical composition of the present invention is an ointment, a paste, a cream and a gel, it may also comprise, besides the alginic acid with low molecular weight and/or its salts of the present invention, conventional carrier substance, such as animal and plant fat, wax, paraffine, starch, tragacanth gum, cellulose derivative, polyethylene glycol, polysiloxane, bentonite, silicon dioxide, talc and zinc oxide, or the mixture thereof.

When the pharmaceutical composition of the present invention is a pulvis and a spray, it may also comprise, besides the alginic acid with low molecular weight and/or its salts of the present invention, conventional carrier substance, such as lactose, talc, silicon dioxide, aluminium hydroxide, calcium silicate and polyamide powder, or the mixture thereof. In addition, the spray may also comprise conventional propellant such as chloro-fluorocarbon.

When the pharmaceutical composition of the present invention is a solution or an emulsion, it may also comprise, besides the alginic acid with low molecular weight and/or its salts of the present invention, conventional carrier substance, such as solvent, solubilizer and emulsifier, for example, water, ethanol, isopropanol, ethyl carbonate, ethyl acetate, benzyl alcohol, benzyl benzoate, propylene glycol, 1,3-butanediol, dimethyl formamide, oil, especially cotton seed oil, peanut oil, corn oil, olive oil, castor oil and sesame oil, glycerol, glycerol formal, tetrahydrofurfuryl alcohol, polyethylene glycol and aliphatic ester of anhydro-sorbit, or the mixture thereof. The solution and emulsion may also exist in sterile and blood-isotonic form, such that they can be used by parenteral route.

When the pharmaceutical composition of the present invention is a suspension, it may also comprise, besides the alginic acid with low molecular weight and/or its salts of the present invention, conventional carrier substance, such as liquid dilute such as water, ethanol and propanediol, suspending agent such as ethoxylated isostearyl, polyoxyethylene sorbitol and sorbitan ester, microcrystalline cellulose, aluminium metahydroxide, bentonite, agar and tragacanth gum, or the mixture thereof.

The pharmaceutical composition of the present invention may also exist in form of a freeze-dry sterile injection formulation, such as water-containing or oil-containing suspension for sterile injection. The suspension can be prepared using appropriate dispersant or wetter (such as Tween 80) and suspending agent by methods known in the art. The sterile injection formulation can be a sterile injection solution or suspension in an avirulent and parenterally compatible dilute or solvent, such as a solution in 1,3-butanediol. The compatible carrier and solvent allowed to be used comprise mannitol, water, Ringer's solution and isotonic solution of sodium chloride. In addition, sterile and non-volatile oil is usually used as solvent or dispersion medium. To this end, any mild and non-volatile oil, including synthetical monoglyceride or diglycerides can be used. Fatty acid, such as oleic acid and its glyceride derivatives can be used in the preparation of the injection formulation, such as natural oil acceptable to the medicament, e.g., olive oil or castor oil, especially, in their polyoxyethylated form. Said oil solution or suspension may also comprise long chain alcohol or similar alcohol as dilute or dispersant.

The pharmaceutical composition of the present invention may also comprise colorant, preservative, odor-taste improving additive, such as peppermint oil and eucalyptus oil, and sweetener such as saccharin.

The pharmaceutical composition may further comprise, besides the alginic acid with low molecular weight and/or its salts of the present invention, other active substances. The pharmaceutical composition is prepared by known methods, such as by mixing alginic acid with low molecular weight and/or its salts (other active substances may also be included) and carrier substances.

For human and animals, the foregoing pharmaceutical compositions can be administered orally, rectally, parenterally (i.e., intravenously, intramuscularly, subcutaneously), intracisternally, intravaginally, intraperitoneally, or topically (powder, paste, drop), and can be used for treatment of inflammation in cavity or body cavity. For oral treatment, injection solution, solution and suspension, gel, brew-up formulation, emulsion, ointment and drop are all appropriate for use. For topical treatment, eyedrops and skin formulation, eardrops, ophthalmic ointment, powder or solution, and implant can be used. For animals, the administration can be conducted with the help of well-formulated feed or drinking water. In addition, gel, powder, tablet, slow release tablet, premix, concentrated formulation, granule, pilule, bolus, capsule, gasoloid, spray and/or inhalant can be used for human and animals. Additionally, the alginic acid with low molecular weight and/or its salts of the present invention can be comprised in other carrier substances, such as plastic (plastic chain for topical treatment), collagen or bone powder.

Preferably, based on the total weight of the pharmaceutical composition, the content of the alginic acid with low molecular weight and/or its salts of the present invention ranges from about 0.1 to about 99.5 wt %, more preferably, about 0.5 to about 95 wt %. More specifically, the content of the alginic acid with low molecular weight and/or its salts ranges from about 60 to about 90 wt %, more preferably, about 65 to about 75 wt % for preparation of oral formulation; and about 30 to about 70 wt %, more preferably, about 45 to about 55 wt % for preparation of suppository. When preparing injection formulation, about 0.5 to about 10 wt %, more preferably, about 8 to about 10 wt % of sodium salt, magnesium salt or sodium potassium salt of the alginic acid with low molecular weight of the present invention is used, wherein the molar ratio of sodium and potassium in the sodium potassium salt can be 4:1. The amount of active substance in single dosage form in the combination with the carrier, i.e., the alginic acid with low molecular weight and/or its salts of the present invention, can be changed by a person skilled in the art according to the patient's recovery situation and administration manner.

The preferable manners for administration of the alginic acid with low molecular weight and/or its salts of the present invention are as follows: granule, powder, tablet, liquid mixture, drop, capsule and so on are preferable for oral administration; suppository, solution and so on are preferable for rectal administration; injection, transfusion and solution, gaseous inhalant, gasoloid, powder and plaster are preferable for parenteral administration; unction, plaster, dressing, lotion and so on are preferable for topical administration. The administration manner of the alginic acid with low molecular weight and/or its salts of the present invention varies according to different diseases, for example, oral administration and injection administration are preferable for treatment of hypertension; colon-soluble capsule and suppository are preferable for treatment of chronic renal failure; and oral administration is preferable for treatment of postprandial hyperglycemia caused by glycosidase.

The alginic acid with low molecular weight and/or its salts of the present invention can be used in a total amount of about 0.05 to about 500 mg/kg of the body, preferably, about 5-about 150 mg/kg of the body weight per 24 hours.

In a preferable embodiment, a daily dose is administrated twice to 5 times, wherein for each administration, 1 to 2 tablets containing about 0.05 to about 150 mg/kg of body weight the alginic acid with low molecular weight and/or its salts of the present invention are used. Of course, a tablet having a higher content, for example, up to 400 mg/kg, of the alginic acid with low molecular weight and/or its salts of the present invention can also be used. The tablet can also be a slow release tablet, wherein the daily administration times reduce to 1 to 4. The content of the alginic acid with low molecular weight and/or its salts of the present invention contained in the slow release tablet can be about 3 to about 300 mg. The alginic acid with low molecular weight and/or its salts of the present invention are preferably administrated for 1 to 8 times per day if they are administrated by injection, or the daily dose is preferably about 1 to about 400 mg if they are administrated via continuous transfusion. This preferable daily dosage is favorable for both human and animals. Sometimes the above dose may be deviated, depending on the subjects' species and body weight, type and degree of disease, formulation type and administration manner, and administration time or interval. Therefore, it is preferable in some situations to contact the pharmaceutical composition in a dose smaller than the above mention dosage with the organism, while it is preferable in some other situations that the above mentioned dosage must be exceeded. A person skilled in the art can easily determine an optimum dose and a proper formulation type of the alginic acid with low molecular weight and/or its salts of the present invention for each case.

The alginic acid with low molecular weight and/or its salts of the present invention are administrated in about 10 to about 400 mg/kg of the body weight, preferably, about 50 to about 300 mg/kg of the body weight for each administration. And the dose for each administration can also be changed by a person skilled in the art. Single dosage preferably includes the amount of the alginic acid with low molecular weight and/or its salts administrated in one administration and the amount of the alginic acid with low molecular weight and/or its salts administrated according to one day, half a day, or ⅓ day, or ¼ day. Therefore, the dosage unit is preferred to be 1, 2, 3, 4 or more times of single dosage, or 0.5, 0.3 or 0.25 of the single dosage. In one preferable embodiment, the daily dose of the alginic acid with low molecular weight and/or its salts of the present invention is administrated 2 to 10 times, preferably, 2 to 7 times, more preferably, 2 to 3 times. Of course, the alginic acid with low molecular weight and/or its salts of the present invention can be administrated by continuous transfusion when they are prepared into injection.

For each oral administration of the alginic acid with low molecular weight and/or its salts of the present invention, about 1 to about 10, preferably, about 4 to about 8, most preferably, about 6 tablets or capsules are used. The tablet according to the present invention may comprise known coating substance and casing, whereby the alginic acid with low molecular weight and/or its salts of the present invention are released at preferable specific locations of the receptor.

The alginic acid with low molecular weight and/or its salts of the present invention can also be used in combination with at least one of the known medicaments, such as calcium channel block (such as amlodipine), diuretic (such as Indapamide, hydrochlorothiazide), β-receptor blocker (such as metoprolol, Propranolol), antihypertensive drug (such as clonidine, dihydroergotamine), angiotensin converting enzyme inhibitor (such as captopril), sodium channel blocker (such as nifedipine), etc. That is to say, the alginic acid with low molecular weight and/or its salts of the present invention can be used together with known medicaments for prevention or treatment of diseases, they can be used together or separately, for example, they can be used in combination of tablet, injection formulation or other known formulations simultaneously or at different times, so as to achieve expected prevention or treatment effects. The said known formulations can be those that can enhance the effects of the alginic acid with low molecular weight and/or its salts of the present invention.

The present invention further provides a pharmaceutical composition for treating hypertension, wherein the said composition comprises an alginic acid with low molecular weight and/or a salt of the alginic acid with low molecular weight and a pharmaceutically acceptable carrier, wherein said alginic acid with low molecular weight is selected from the alginic acid with low molecular weight according to the present invention; Said salt of the alginic acid with low molecular weight is selected from the salts of the alginic acid with low molecular weight according to the present invention, and the weight average molecular weight of said alginic acid with low molecular weight ranges from about 800 to about 2,500 Da. Based on the total weight of the pharmaceutical composition, the content of the alginic acid with low molecular weight and/or the salt of the alginic acid with low molecular weight ranges from about 0.5 to about 99.5 wt %. When preparing injection formulation, the content of the alginic acid with low molecular weight and/or its salts is preferably about 0.5 to about 10 wt %, more preferably, about 8 to about 10 wt % based on the total weight of the pharmaceutical composition. The pharmaceutically acceptable carrier comprises one or more selected from injection class water, injection class propanediol, injection class polyethylene glycol, sodium chloride, sodium bicarbonate, sodium bisulfite, disodium edentate, potassium chloride and glucose. Based on the total weight of the pharmaceutical composition, the content of the pharmaceutically acceptable carrier can be about 90 to about 99 wt % for injection class water, about 0 to about 15 wt % for injection class propanediol, about 0 to about 16 wt % for injection class polyethylene glycol, about 0 to about 0.9 wt % for sodium chloride, about 0 to about 0.8 wt % for sodium bicarbonate, about 0 to about 0.8 wt % for sodium bisulfite, about 0 to about 6 wt % for disodium edentate, about 0 to about 0.5 wt % for potassium chloride and about 0 to about 10 wt % for glucose. When the pharmaceutical composition containing about 10 wt % of the alginic acid with low molecular weight and/or its salts of the present invention is administrated by injection or transfusion, the effective dose for treating hypertension is about 20 to about 300 mg/Kg of the body weight, more preferably, about 30 to about 150 mg/Kg, of the body weight per 24 hours. When preparing an oral formulation, the content of the alginic acid with low molecular weight and/or its salts ranges preferably from about 60 to about 90 wt %, more preferably, about 65 to about 75 wt % based on the total weight of the pharmaceutical composition. The pharmaceutically acceptable carrier comprises one or more selected from starch, dextrine, sucrose powder, lactose, glucose, calcium sulphate, calcium carbonate, calcium hydrophosphate, aluminium hydroxide, magnesium aluminum sulfate, water, ethanol, acrylic resin, polyvidone, gelatin, croscarmellose sodium, cellulose, polyethylene glycol, sodium dodecyl sulfonate, stearic acid, magnesium stearate and calcium stearate, wherein the acrylic resin is preferably one or more selected from methacrylic acid/methyl acrylate copolymer, methacrylic acid/methyl methacrylate copolymer, methacrylic acid/ethyl acrylate copolymer and methacrylic acid/ethyl methacrylate copolymer, methacrylic acid/acrylate copolymer and methacrylic acid/methacrylate copolymer. Based on the total weight of the pharmaceutical composition, the content of the pharmaceutically acceptable carrier can be about 0 to about 50 wt % for starch, about 0 to about 10 wt % for dextrine, about 0 to about 20 wt % for sucrose powder, about 0 to about 20 wt % for lactose, about 0 to about 15 wt % for glucose, about 0 to about 2 wt % for calcium sulphate, about 0 to about 3 wt % for calcium carbonate, about 0 to about 2 wt % for calcium hydrophosphate, about 0 to about 2 wt % for aluminium hydroxide, about 0 to about 3 wt % for magnesium aluminum sulfate, about 0 to about 10 wt % for water, about 0 to about 20 wt % for ethanol, about 0 to about 25 wt % for acrylic resin, about 0 to about 10 wt % for polyvidone, about 0 to about 35 wt % for gelatin, about 0 to about 10 wt % for croscarmellose sodium, about 0 to about 10 wt % for cellulose, about 0 to about 30 wt % for polyethylene glycol, about 0 to about 2 wt % for sodium dodecyl sulfonate, about 0 to about 5 wt % for stearic acid, about 0 to about 2 wt % for magnesium stearate and about 0 to about 2 wt % for calcium stearate. When the pharmaceutical composition containing about 100 wt % of the alginic acid with low molecular weight and/or its salts of the present invention (such as a dried granule prepared with water) is orally administrated, the effective dose for treating hypertension is about 25 to about 350 mg/Kg of the body weight, more preferably, about 50 to about 150 mg/Kg, of the body weight per 24 hours. When the pharmaceutical composition containing about 60 wt % of the alginic acid with low molecular weight and/or its salts of the present invention is orally administrated, the effective dose for treating hypertension is about 25 to about 400 mg/Kg, more preferably, about 50 to about 200 mg/Kg, of the body weight per 24 hours. It should be explained that "effective" means that the systolic blood pressure reduces by more than about 15 mmHg and the diastolic blood pressure reduces by more than about 10 mmHg 24 hours after the administration (refer to the criterion of therapeutical effect made by China Hypertension League).

The present invention further provides a pharmaceutical composition for treating chronic renal failure, wherein the said composition comprises an alginic acid with low molecular weight and a pharmaceutically acceptable carrier, wherein said alginic acid with low molecular weight is selected from the alginic acid with low molecular weight according to the present invention, having a weight average molecular weight ranging from about 2,500 to about 4,500 Da. Based on the total weight of the pharmaceutical composition, the content of the alginic acid with low molecular weight ranges from about 0.5 to about 99.5 wt %. When preparing a pharmaceutical composition that is intrarectally administrated, the content of the alginic acid with low molecular weight ranges preferably from about 30 to about 70 wt % based on the total weight of the pharmaceutical composition. When preparing a suppository, the pharmaceutically acceptable carrier comprises one or more selected from cocoa butter, fatty glyceride, polyethylene glycol, glycerogelatin, acrylic resin, polyoxyethylene monostearate and poloxamer. Based on the total weight of the pharmaceutical composition, the content of the pharmaceutically acceptable carrier can be about 0 to about 20 wt % for cocoa butter, about 0 to about 15 wt % for fatty glyceride, about 0 to about 25 wt % for polyethylene glycol, about 0 to about 35 wt % for glycerogelatin, about 0 to about 35 wt % for acrylic resin, about 0 to about 15 wt % for polyoxyethylene monostearate and about 0 to about 10 wt % for poloxamer. The acrylic resin is preferably one or more selected from methacrylic acid/methyl acrylate copolymer, methacrylic acid/methyl methacrylate copolymer, methacrylic acid/ethyl acrylate copolymer and methacrylic acid/ethyl methacrylate copolymer, methacrylic acid/acrylate copolymer and methacrylic acid/methacrylate copolymer. When a pharmaceutical composition suppository containing about 70 wt % of the alginic acid with low molecular weight and/or its salts of the present invention is administrated, the effective dose for treating chronic renal failure is about 50 to about 500 mg/Kg, preferably, about 100 to about 200 mg/Kg, more preferably, about 200 to about 500 mg/K, of the body weight per 24 hours. It should be explained that "effective" means that the blood urea nitrogen value reduces by at least about 10 mmol/L and the serum creatinine reduces by at least about 100 μmol/L 24 hours after the administration.

When preparing an oral formulation, the content of the alginic acid with low molecular weight is preferably about 60 to about 90 wt %, more preferably, about 65 to about 75 wt % based on the total weight of the pharmaceutical composition. The pharmaceutically acceptable carrier comprises one or more selected from starch, dextrine, sucrose powder, lactose, glucose, calcium sulphate, calcium carbonate, calcium hydrophosphate, aluminium hydroxide, magnesium aluminum sulfate, water, ethanol, acrylic resin, polyvidone, gelatin, croscarmellose sodium, cellulose, polyethylene glycol, sodium dodecyl sulfonate, stearic acid, magnesium stearate and calcium stearate, wherein the acrylic resin is preferably one or more selected from the group consisting of methacrylic acid/methyl acrylate copolymer, methacrylic acid/methyl methacrylate copolymer, methacrylic acid/ethyl acrylate copolymer, methacrylic acid/ethyl methacrylate copolymer, methacrylic acid/acrylate copolymer and methacrylic acid/methacrylate copolymer. Based on the total weight of the pharmaceutical composition, the content of the pharmaceutically acceptable carrier can be about 0 to about 50 wt % for starch, about 0 to about 10 wt % for dextrine, about 0 to about 20 wt % for sucrose powder, about 0 to about 20 wt % for lactose, about 0 to about 15 wt % for glucose, about 0 to about 2 wt % for calcium sulphate, about 0 to about 3 wt % for calcium carbonate, about 0 to about 2 wt % for calcium hydrophosphate, about 0 to about 2 wt % for aluminium hydroxide, about 0 to about 3 wt % for magnesium aluminum sulfate, about 0 to about 10 wt % for water, about 0 to about 20 wt % for ethanol, about 0 to about 25 wt % for acrylic resin, about 0 to about 10 wt % for polyvidone, about 0 to about 35 wt % for gelatin, about 0 to about 10 wt % for croscarmellose sodium, about 0 to about 10 wt % for cellulose, about 0 to about 30 wt % for polyethylene glycol, about 0 to about 2 wt % for sodium dodecyl sulfonate, about 0 to about 5 wt % for stearic acid, about 0 to about 2 wt % for magnesium stearate and about 0 to about 2 wt % for calcium stearate. When a pharmaceutical composition suppository containing about 70 wt % of the alginic acid with low molecular weight of the present invention administrated, the effective dose for treating chronic renal failure is about 30 to about 300 mg/Kg, preferably, about 50 to about 200 mg/Kg, of the body weight per 24 hours. It should be explained that "effective" means that the blood urea nitrogen value reduces by at least about 10 mmol/L and the serum creatinine reduces by at least about 100 μmol/L 24 hours after the administration.

The present invention further provides a pharmaceutical composition for treating postprandial hyperglycemia caused by glycosidase, wherein the said composition comprises an alginic acid with low molecular weight and/or a salt of the alginic acid with low molecular weight and a pharmaceutically acceptable carrier. Said alginic acid with low molecular weight is selected from the alginic acid with low molecular weight according to the present invention. Said salt of the alginic acid with low molecular weight is selected from the salts of the alginic acid with low molecular weight according to the present invention. The weight average molecular weight of said alginic acid with low molecular weight ranges preferably from about 1,000 to about 4,500 Da, more preferably, about 1,000 to about 3,000 Da. Based on the total weight of the pharmaceutical composition, the content of the alginic acid with low molecular weight and/or its salts ranges from about 0.5 to about 99.5 wt %, preferably, about 60 to about 90 wt %. When preparing an oral formulation, the pharmaceutically acceptable carrier comprises one or more selected from starch, dextrine, calcium sulphate, calcium carbonate, calcium hydrophosphate, aluminium hydroxide, magnesium aluminum sulfate, water, ethanol, acrylic resin, polyvidone, gelatin, croscarmellose sodium, cellulose, polyethylene glycol, sodium dodecyl sulfonate, stearic acid, magnesium stearate and calcium stearate, wherein the acrylic resin is preferably one or more selected from the group consisting of methacrylic acid/methyl acrylate copolymer, methacrylic acid/methyl methacrylate copolymer, methacrylic acid/ethyl acrylate copolymer and methacrylic acid/ethyl methacrylate copolymer, methacrylic acid/acrylate copolymer and methacrylic acid/methacrylate copolymer. Based on the total weight of the pharmaceutical composition, the content of the pharmaceutically acceptable carrier can be about 0 to about 50 wt % for starch, about 0 to about 10 wt % for dextrine, about 0 to about 5 wt % for calcium sulphate, about 0 to about 5 wt % for calcium carbonate, about 0 to about 3 wt % for calcium hydrophosphate, about 0 to about 3 wt % for aluminium hydroxide, about 0 to about 3 wt % for magnesium aluminum sulfate, about 0 to about 10 wt % for water, about 0 to about 20 wt % for ethanol, about 0 to about 10 wt % for acrylic resin, about 0 to about 10 wt % for polyvidone, about 0 to about 25 wt % for gelatin, about 0 to about 10 wt % for croscarmellose sodium, about 0 to about 10 wt % for cellulose, about 0 to about 25 wt % for polyethylene glycol, about 0 to about 1 wt % for sodium dodecyl sulfonate, about 0 to about 5 wt % for stearic acid, about 0 to about 2 wt % for magnesium stearate and about 0 to about 1 wt % for calcium stearate. When the pharmaceutical composition containing about 70 wt % of the alginic acid with low molecular weight and/or its salts of the present invention administrated, the effective dose for treating postprandial hyperglycemia caused by glycosidase is about 50 to about 400 mg/Kg, preferably, about 100 to about 300 mg/Kg, of the body weight per 24 hours. It should be explained that "effective" means that the postprandial blood glucose reduces by at least about 2 mmol/L one to two hours after the administration.

The present invention further provides a health food containing the alginic acid with low molecular weight and/or the salt of the alginic acid with low molecular weight of the present invention. The alginic acid with low molecular weight and/or its salts of the present invention can be added to various foods, such as dairy product (such as fresh milk, milk powder, yoghourt, milk drink, cheese and butter, milk partner, etc), common beverage (such as mineral water, purified water, Fruit juice, coffee, soy milk, cola, etc), nutrition supplement (such as vitamin supplement, amino acid supplement, microelement supplement, etc), functional beverage (such as anti-fatigue beverage, immunity increasing beverage), staple food (such as cake, bread, flour, butter, pulse flour, sesame seed powder), flavouring (such as salt, soy sauce, essence of chicken, monosodium glutamate, honey, etc). The addition level of the alginic acid with low molecular weight and/or its salts of the present invention can be adjusted according to daily consumption of the foods, for example, the additional level can be: about 0.5 to about 12 g for solid dairy product (such as milk powder) and staple food whose daily consumption is about 0.5 to about 1,000 g; about 0.5 to about 12 mg for liquid dairy product (such as fresh milk and yogurt) whose daily consumption is about 50 to about 1,000 ml; about 0.5 to about 12 g for common beverage (such as mineral water, purified water, Fruit juice, coffee, soy milk, cola, etc) whose daily consumption is about 10 to about 1,000 ml; about 0.1 to about 12 g for solid flavouring whose daily consumption is about 1 to about 12 g; and about 0.1 to about 12 g for liquid flavouring whose daily consumption is about 10 to about 1,000 ml.

Unless otherwise specified, the various reagents used in the present invention are all commercially available or can be prepared by conventional methods employed in the art. In addition, the reagents for preparation of the pharmaceutical composition are not only required to be pure, preferably, analytically pure, but also should not contain any substance that affect normal biophysical activity of animals or human, therefore, said reagents should meet the requirements of medical product, so, injection class bulk pharmaceutical chemicals are preferable. The present invention is further explained according to the following examples.

Example 1

This example explains the alginic acid with low molecular weight and its salt of the present invention, and preparative method thereof.

1) Measurement of Alginic Acid Raw Material 20 mg *Sargassum hemiphyllum* used as raw material was cut into pieces and 800 ml $Na_2CO_3$ solution (1%) was added, followed by an extraction at 75° C. for one hour, then the solution was filtered to obtain filtered liquor, and then, diluted hydrochloric acid (2 mol/L) was added into the filtered liquor with the filtered liquor being stirred until the pH value reached 2, then the produced alginic acid was filtered out and washed with distilled water for three times, thereafter, proper amount of NaOH (2%) was added while being stirred until the pH value reached 7.5 and the alginic acid was completely dissolved, and then hydrochloric acid (1 mol/L) was used to adjust the pH value to 7.0 to obtain a sodium alginate solution. The obtained solution was measured using the combination of mini DAWN TREOS laser light scattering instrument of American Wyatt Company (WTC), and 150c, PL220c and ALLIANCE 2000 of American Waters Company according to their instructions to measure the molecular weight and molecular weight distribution of the alginic acid raw material (i.e., *Sargassum hemiphyllum*), the results were obtained by averaging three samples and showed that the alginic acid weight-average molecular weight of the *Sargassum hemiphyllum* was 200,000 Da. Guluronic acid unit and mannuronic acid unit were quantified according to colorimetric method described in *Biochemical Research Technique of Complex Carbohydrate*, Zhang Weijie, Zhejiang University Press, $2^{nd}$ edition, 1999, p 342, the results obtained by averaging three samples showed that the molar ratio of the guluronic acid unit to mannuronic acid unit was 0.8.

2) Degradation of Alginic Acid Raw Material

As measured in above step 1), the alginic acid raw material has a weight-average molecular weight of the *Sargassum hemiphyllum* of 200,000 Da, and a G to M molar ratio of 0.8. 1 kg of said alginic acid raw material was ground into about 0.5 $mm^3$ and then degraded in a 10 volume of diluted hydrochloric acid having a final concentration of 0.45 mol/L at 93° C. under a pressure of 0.10 Mpa for 6 hours.

3) Separation and Collection of Alginic Acid with Low Molecular Weight

The precipitate was collected after 15 minutes of centrifuging at 10,000 rpm and then was washed with 20 L ethanol (95%), thereafter, the washed precipitate was collected after 10 minutes of centrifuging at 10,000 rpm, and then the precipitate was dried under a 50 mmHg vacuum condition to obtain 750 g powdery alginic acid product with low molecular weight. The yield of the alginic acid with low molecular weight was calculated to be 75% according to the following formula:

Yield=100%×the weight of alginic acid product(g)/the weight of alginic acid raw material(g).

4) Measurement of Alginic Acid with Low Molecular Weight 50 g alginic acid with low molecular weight powder product obtained in above step 3) was dropwise added with sodium hydroxide aqueous solution (1 mol/L) until the pH value reached 7.0 and the alginic acid was converted into low molecular weight sodium alginate solution. The obtained solution was measured using the combination of mini DAWN TREOS laser light scattering instrument of American Wyatt Company (WTC), and 150c, PL220c and ALLIANCE 2000 of American Waters Company according to their instructions to measure the molecular weight and molecular weight distribution of the alginic acid with low molecular weight, the results were obtained by averaging three samples and showed that the alginic acid weight-average molecular weight of the alginic acid with low molecular weight was about 4,500 Da (in term of sodium alginate, hereafter the same). Guluronic acid unit and mannuronic acid unit were quantified according to colorimetric method described in Biochemical Research Technique of Complex Carbohydrate, Zhang Weijie, Zhejiang University Press, $2^{nd}$ edition, 1999, p 342, and the results obtained by averaging three samples showed that the G to M molar ratio was 1.0.

5) Preparation, Separation and Collection of Low Molecular Weight Alginate 500 g alginic acid with low molecular weight obtained in above step 3) was stirred and mixed with potassium hydroxide aqueous solution (10 wt %) according to a molar ratio of 1:1 (alginic acid:potassium hydroxide), the pH value reached 7.5 and then hydrochloric acid (1 mol/L) was used to adjust the pH value to 7.0. Thereafter, 50 L ethanol (95%) was added, followed by a precipitation for 12 hours, then the precipitate was collected after 10 minutes of centrifuging at 10,000 rpm, and the precipitate was then dried under a 50 mmHg vacuum condition to obtain a powdery low molecular weight potassium alginate product.

The foregoing measurement steps 1) and 4) are not necessary for carrying out the present invention, more specifically, when a batch of alginic acid raw material goes through the measurement step 1), the alginic acid raw material that is measured to be qualified can be directly used to complete the present invention later on; and the measurement step 4) is for explaining the properties of the alginic acid with low molecular weight or the salt of the alginic acid with low molecular weight of the present invention, that is, the weight-average molecular weight and the G to M molar ratio.

Example 2

This example explains the alginic acid with low molecular weight and its salt of the present invention, and preparative method thereof.

1) Primary Degradation 1.5 kg alginic acid raw material same with that used in example 1 was ground into about 0.4 $mm^3$ and then added with 9 L deionized water to form a slurry, followed by an ultrasonic treatment for 3 hours using American Sonic & Materials 1500 ultrasonic equipment having a total power of 1,500 W and a working frequency of 20 kHz. The product of the ultrasonic treatment was then maintained at a temperature ranging from 120 to 122° C. under 0.25 MPa for 3 hours and thereafter cooled to room temperature. 100 g degradation product was measured according to the step 4) of example 1, and the results measured showed that the product of primary degradation has a weight-average molecular weight of 20,000 Da.

2) Degradation by Diluted Acid 1 kg primary degradation product of step 1) was degraded in a diluted hydrochloric acid having a final concentration of 0.5 mol/L at 85° C. under a pressure of 0.10 Mpa for 2 hours.

The total weight of the alginic acid with low molecular weight collected according to the method of example 1 was 1180 g and it was measured that the alginic acid has a weight-average molecular weight of 3,000 Da and a G to M molar ratio of 1.5. The yield of the alginic acid with low molecular weight was 78.7%.

3) Preparation, Separation and Collection of Low Molecular Weight Alginate Salts Sodium alginate was prepared according to the method described in example 1, except that the alkaline substance was sodium hydroxide (10 wt %).

Example 3

This example explains the alginic acid with low molecular weight and its salt of the present invention, and preparative method thereof. The alginic acid raw material used in this example was pharmaceutical grade alginic acid approved by the state and produced by Dalian Seaweed Industries, China.

1) Primary Degradation

Primary degradation was conducted according to the method described in the first stage of example 2 disclosed in PCT/CN99/00202. More specifically, 500 g of said acid pharmaceutical grade alginic acid was added with distilled water and evenly stirred until the alginic acid became 9% of the total weight of the water. The mixture was heated to 40 to 50° C., and then dropwise added with hydrogen peroxide solution (30%) while being stirred until the final concentration of the hydrogen peroxide in the system reached 1% of the total weight. The mixture reacted for 2 hours while being stirred, and the temperature was increased to over 80° C. to remove the unreacted hydrogen peroxide through decomposition. Thereafter, the alginic acid treated with hydrogen peroxide solution was dropwise added with potassium hydroxide (30%) while being stirred, and suitable amount of distilled water was added to dissolve the product thoroughly, finally, the system pH value was kept between 6 to 7. Measured by the method according to example 1, the product has a weight average molecular weight of 6,500 Da and a G to M molar ratio of 1.0.

2) Degradation by Diluted Acid 1 kg primary degradation product of step 1) was degraded in a diluted hydrochloric acid having a final concentration of 0.4 mol/L at 90° C. under a pressure of 0.09 Mpa for 1 hour.

The total weight of the alginic acid with low molecular weight collected according to the method of example 1 was 780 g and it was measured that the alginic acid has a weight-average molecular weight of 3,000 Da and a G to M molar ratio of 2.5. The yield of the alginic acid with low molecular weight was 78%.

3) Preparation, Separation and Collection of Low Molecular Weight Alginate

Ammonium alginate was prepared according to the method described in example 1, except that the alkaline substance was ammonia (10 wt %).

Example 4

This example explains the alginic acid with low molecular weight and its salt of the present invention, and preparative method thereof.

1) Primary Degradation 1.5 kg alginic acid raw material same with that used in example 1 was applied with ultrasonic treatment according to the primary degradation method described in example 2, and the obtained primary degradation product was then applied with oxidative degradation according to the primary degradation method described in example 3.

2) Degradation by Diluted Acid

The final degradation product from above step 1) was degraded in a diluted hydrochloric acid having a final concentration of 0.3 mol/L at 85° C. under a pressure of 0.08 Mpa for 0.5 hour.

The total weight of the alginic acid with low molecular weight collected according to the method of example 1 was 870 g and it was measured that the alginic acid has a weight-average molecular weight of 1,500 Da and a G to M molar ratio of 1.0. The yield of the alginic acid with low molecular weight was 58%.

3) Preparation, Separation and Collection of Low Molecular Weight Alginate

Ammonium alginate was prepared according to the method described in example 1, except that the alkaline substance was ammonia (10 wt %).

Examples 5-10

These examples explain the alginic acid with low molecular weight and its salts of the present invention, and preparative method thereof.

The alginic acid with low molecular weight and its salts were prepared according to the method of example 2, wherein the preparation conditions and the measurement results of the prepared alginic acid with low molecular weight were shown in the following Table 1.

TABLE 1

| | example | | | | | |
|---|---|---|---|---|---|---|
| | example 5 | example 6 | example 7 | example 8 | example 9 | example 10 |
| Hydrogen ion concentration (mol/L) | 0.3 | 0.4 | 0.4 | 0.45 | 0.45 | 0.5 |
| temperature (° C.) | 95 | 85 | 90 | 100 | 100 | 100 |
| pressure (Mpa) | 0.08 | 0.09 | 0.10 | 0.11 | 0.12 | 0.13 |
| Degradation time (hour) | 1 | 2 | 3 | 1 | 2 | 3 |
| weight-average molecular weight (Da) | 3500 | 1800 | 1500 | 2000 | 1100 | 800 |
| G/M molar ratio | 1.4 | 2.6 | 2.8 | 5 | 10 | 18 |
| Yield %) | 78 | 48 | 45 | 50 | 42 | 21 |

Comparative Example 1

This comparative example explains the alginic acid with low molecular weight and its salt of the present invention, and preparative method thereof in the prior art.

Alginic acid with low molecular weight or its salt were prepared using the alginic acid same with that used in example 1 according to the method described in example 2 of PCT/CN99/00202. Measured by the method according to example 1, the prepared alginic acid with low molecular weight has a weight average molecular weight of 6,500 Da and a G to M molar ratio 0.8. The yield of the alginic acid with low molecular weight was 30%.

Example 11

This example explains the pharmaceutical compositions of the present invention, and preparative method thereof.

The alginic acid with low molecular weight and/or its salts prepared by examples 1-10 were prepared into granule, enteric capsule, colon-soluble capsule, suppository and injection according to the following formula and method.

1) Granules

Alginic acid with low molecular weight or its salt was mixed with distilled water according to a weight ratio of 1:4, then the mixture was made into damp mass and passed through a 16-mesh nylon screen to produce granules, the granules were then dried under 60° C. to a constant weight, pelletizing the granules. The content of the alginic acid with low molecular weight or its salt in the obtained granule was 99.5%.

2) Enteric Capsules

Each of 0.5 g alginic acid with low molecular weight or its salt was placed into an enteric capsule (manufactured by Chaozhou Qiangji Pharmaceutical Factory, Guangdong, China) to obtain the enteric capsule according to the present invention, wherein the material for said enteric capsule was a methacrylic acid/ethyl acrylate (1:1) copolymer, and the content of alginic acid with low molecular weight or its salt in the enteric capsule was 85%.

3) Colon-Soluble Capsules

Each of 0.4 g alginic acid with low molecular weight or its salt was placed into an Colon-soluble capsule (manufactured by Chaozhou Qiangji Pharmaceutical Factory, Guangdong, China) to obtain the colon-soluble capsule according to the present invention, wherein the material for said colon-soluble capsule was a methacrylic acid/methyl methacrylate (1:2) copolymer, and the content of alginic acid with low molecular weight or its salt in the colon-soluble capsule was 75%.

4) Microcapsule

Modified starch octenyl succinate edible microcapsule embedding agent (manufactured by Chaozhou Qiangji Pharmaceutical Factory, Guangdong, China) was added with 12 volume of distilled water having a room temperature, the mixture was stirred to be homogeneous, and the powder of the alginic acid with low molecular weight or its salt of the present invention was gradually added into the mixture, thereafter, the mixture was continuously stirred to be homogeneous, finally, the mixture was spray-dried at 165° C. The weight ration between the powder of the alginic acid with low molecular weight or its salt of the present invention and the modified starch octenyl succinate edible microcapsule embedding agent was 2:1, and the content of alginic acid with low molecular weight or its salt in the microcapsule was 66%.

5) Suppositories

A substrate consisting of 220 g PEG-4000, 310 g PEG-6,000, 50 g glycerol and 200 ml water was molten and gradually added with 250 g powder of the alginic acid with low molecular weight or its salt and mixed with the same evenly, then the mixture was quickly poured into a rectal suppository mold coated with plant oil lubricant, the unnecessary portions on the mold was peeled with a knife after the mold was cooled, and then the suppository mold was opened. The content of alginic acid with low molecular weight or its salt in the suppository was 40%.

6) Injections

Low molecular weight alginate salt was dissolved in pyrogen-free injection water according to a weight ratio of 1:10, the pH value was adjusted to 7.0 to 7.5 using citric acid, the solution was then filtered using a 0.22 μm filter membrane, and thereafter the filtered liquor was sub-packaged and sterilized in 15 pounds per 30 minute at 121.3° C. The injection water and the citric acid were both went through depyrogenation treatment. And the low molecular weight alginate salt contained in the injection water was 4%.

Comparative Example 2

The alginic acid with low molecular weight and/or its salt according to comparative example 1 were prepared into granule, enteric capsule, colon-soluble capsule, suppository and injection according to the same method as described in example 11.

Clinical Example 1

This clinical example explains the effects of the low molecular weight alginate salts of the present invention and the effects of the low molecular weight alginate salts of the comparative example in improving hypertension.

Measuring Method:

Male and female hypertension subjects without other disease were selected, 360 for each sex, aged from 38 to 62 with an average age of 48, whose systolic blood pressure (SBP)(s) were from 155 to 165 mmHg and diastolic blood pressure (DBP)(s) were from 100 to 125 mmHg, said SBP(s) and DBP(s) were measured in resting state. The subjects were randomly grouped, 30 subjects for each group, and orally took granule of low molecular weight potassium alginate or enteric capsule of alginic acid with low molecular weight 1 to 3 times per day with a daily dose of 50 to 200 mg/Kg according to Table 2, and blood pressures before and 24 hours after administration were measured. The granule of low molecular weight potassium alginate was prepared in the following way: potassium alginate was prepared using the alginic acid with low molecular weight according to examples 1 to 10 or comparative example 1, and then the potassium alginate was prepared into granule according to the method of example 11 or comparative example 2. The enteric capsule of alginic acid with low molecular weight was prepared according to the method of example 11 or comparative example 2. Criterion of therapeutical effect made by China Hypertension League was referred to, that is, the systolic blood pressure reduces by more than 15 mmHg and the diastolic blood pressure reduces by more than 10 mmHg 24 hours after the administration. Hydrochlorothiazide tablet (25 mg per tablet, manufactured by Tianjin Lisheng Pharmaceutical Co., Ltd) was used as positive control drug. The results are shown in the following Table 2.

TABLE 2

| Administrated medicament | Daily taken times | Daily dose (mg/Kg) | weight-average molecular weight | G/M molar ratio | average SBP/DBP before administration (mmHg) | average SBP/DBP after administration 24 h (mmHg) | effective rate (%) |
|---|---|---|---|---|---|---|---|
| Example 1 Granules | 3 | 200 | 4500 | 1.0 | 160/110 | 125/95 | 81.3 |
| Example 2 Granules | 3 | 200 | 3000 | 1.5 | 158/111 | 124/94 | 83.3 |
| Example 3 Granules | 3 | 150 | 3000 | 2.5 | 163/112 | 122/93 | 86.6 |
| Example 4 Granules | 2 | 150 | 1500 | 1.0 | 160/110 | 121/92 | 84.3 |
| Example 5 Granules | 2 | 200 | 3500 | 1.4 | 162/113 | 123/93 | 82.5 |
| Example 6 Granules | 2 | 150 | 1800 | 2.6 | 162/112 | 122/92 | 86.5 |
| Example 7 Granules | 2 | 100 | 1500 | 2.8 | 161/110 | 121/92 | 88.6 |
| Example 8 Granules | 2 | 90 | 2000 | 5 | 162/109 | 122/85 | 90.0 |
| Example 9 Granules | 1 | 50 | 1100 | 10 | 162/118 | 120/80 | 93.9 |
| Example 10 Granules | 2 | 80 | 800 | 18 | 164/120 | 120/80 | 94.1 |
| Comparative Example 1 Granules | 3 | 200 | 6500 | 0.8 | 163/116 | 127/95 | 80.0 |
| Example 1 Enteric Capsules | 3 | 200 | 4500 | 1.0 | 161/110 | 127/96 | 72.5 |
| Example 2 Enteric Capsules | 3 | 200 | 3000 | 1.5 | 159/112 | 125/95 | 74.5 |
| Example 3 Enteric Capsules | 3 | 150 | 3000 | 2.5 | 163/120 | 123/94 | 78.3 |
| Example 4 Enteric Capsules | 2 | 150 | 1500 | 1.0 | 160/121 | 122/93 | 75.1 |
| Example 5 Enteric Capsules | 2 | 200 | 3500 | 1.4 | 162/123 | 124/92 | 72.9 |
| Example 6 Enteric Capsules | 2 | 150 | 1800 | 2.6 | 161/119 | 123/93 | 77.3 |
| Example 7 Enteric Capsules | 2 | 100 | 1500 | 2.8 | 161/118 | 122/93 | 79.3 |
| Example 8 Enteric Capsules | 2 | 90 | 2000 | 5 | 162/119 | 123/86 | 81.7 |
| Example 9 Enteric Capsules | 1 | 50 | 1100 | 10 | 160/118 | 120/81 | 85.3 |
| Example 10 Enteric Capsules | 2 | 80 | 800 | 18 | 160/116 | 120/81 | 85.8 |
| Comparative Example 1 Enteric Capsules | 3 | 200 | 6500 | 0.8 | 160/117 | 130/97 | 70.6 |
| Positive Control | 3 | 2 | — | — | 162/118 | 121/95 | 70.1 |

According to table 2, the granule of the low molecular weight potassium alginate of the present invention or the enteric capsule of the alginic acid with low molecular weight of the present invention is effective in reducing blood pressure, moreover, subject to the condition that the molecular weights were the same, the greater the G/M value is, the greater the said effects would be, and its effect is not only higher than positive control hydrochlorothiazide tablet, but also higher than the granule of the low molecular weight potassium alginate of the comparative example 1 or the enteric capsule of the alginic acid with low molecular weight of the comparative example 1.

Clinical Example 2

This clinical example explains the effects of the alginic acid with low molecular weight of the present invention and the effects of the alginic acid with low molecular weight of the comparative example in relieving chronic renal failure.

Measuring Method:

Male and female chronic renal failure subjects, without other disease or complications were selected, 48 for each sex, aged from 50 to 62 with an average age of 56, each of whom was in azotemia stage in which the glomerular filtration rate reduced to 25 ml/min, nephrons reduced by 50% to 70% and there was kidney concentration dysfunction. The subjects were randomly grouped, 8 for each group, and orally took colon-soluble capsule of alginic acid with low molecular weight 3 times per day with a daily dose of 100 to 400 mg/Kg according to Table 3, serum creatinine and urea nitrogen changes were measured 24 hours after administration. The colon-soluble capsule of alginic acid with low molecular weight was prepared by using the alginic acid with low molecular weight according to examples 1-10 by the method according to example 11 or comparative example 2. It should be explained that "effective" means that the blood urea nitrogen reduces by at least 10 mmol/L and the serum creatinine reduces by at least 100 μmol/L 24 hours after the administration. Coated Aldehyde Oxystarch capsule (0.625 gram per capsule, manufactured by Tianjin Pacific Pharmaceutical Co., Ltd) was used as positive control drug.

The results are shown in the following Table 3.

TABLE 3

| Administrated medicament | Daily taken times | Daily dose (mg/Kg) | Weight-average molecular weight | G/M molar ratio | Creatinine reduction after administration ($\mu$mol/L) | Blood urea nitrogen reduction after administration (mmol/L) | Effective rate (%) |
|---|---|---|---|---|---|---|---|
| Example 1 Alginic Acid Colon-soluble Capsule | 3 | 150 | 4500 | 1.0 | 117 | 18 | 78 |
| Example 2 Alginic Acid Colon-soluble Capsule | 1 | 300 | 3000 | 1.5 | 114 | 15 | 77 |
| Example 3 Alginic Acid Colon-soluble Capsule | 3 | 300 | 3000 | 2.5 | 117 | 17 | 78 |
| Example 4 Alginic Acid Colon-soluble Capsule | 2 | 350 | 1500 | 1.0 | 112 | 12 | 72 |
| Example 5 Alginic Acid Colon-soluble Capsule | 3 | 300 | 3500 | 1.4 | 113 | 14 | 76 |
| Example 6 Alginic Acid Colon-soluble Capsule | 3 | 300 | 1800 | 2.6 | 107 | 13 | 71 |
| Example 7 Alginic Acid Colon-soluble Capsule | 2 | 350 | 1500 | 2.8 | 110 | 13 | 73 |
| Example 8 Alginic Acid Colon-soluble Capsule | 3 | 300 | 2000 | 5 | 113 | 14 | 75 |
| Example 9 Alginic Acid Colon-soluble Capsule | 1 | 400 | 1100 | 10 | 111 | 12 | 72 |
| Example 10 Alginic Acid Colon-soluble Capsule | 3 | 400 | 800 | 18 | 105 | 11 | 71 |
| Comparative Example 1 Alginic Acid Colon-soluble Capsule | 3 | 400 | 6500 | 0.8 | 100 | 10 | 66 |
| Positive Control | 3 | 400 | — | — | 101 | 11 | 71 |

According to table 3, the colon-soluble capsule of the alginic acid with low molecular weight of the present invention is effective in reducing creatinine and blood urea nitrogen of patients with chronic renal failure, moreover, subject to the condition that the molecular weights were the same, the greater the G/M value is, the greater the said effects would be, and its effect is comparable to that of the positive control, oxyamyli *tectus* aldehydum (coated aldehyde oxystarch) and is much better than that of the colon-soluble capsule of the alginic acid of the comparative example 1.

Clinical Example 3

This clinical example explains the effects of the alginic acid with low molecular weight of the present invention and the effects of the alginic acid with low molecular weight of the comparative example in relieving chronic renal failure.

Measuring Method:

80 chronic renal failure rat models were prepared according to method disclosed in Experiment Research on Treating Rats with CRF Caused by Adenine with Shenshuaining Dispersible Tablets, Ma Yun, et. al, Chinese Medicinal Plant, Vol. 30, No. 4, P 432-435, 2007, the models were randomly grouped, 8 for each group, and were rectally administrated with suppository of alginic acid with low molecular weight three times per day with a daily dose of 200 to 500 mg/Kg according to Table 4, serum creatinine and urea nitrogen changes were measured 24 hours after administration. The suppository of alginic acid with low molecular weight was prepared by using the alginic acid with low molecular weight according to examples 1-10 by the method according to example 11 or comparative example 2. It should be explained that "effective" means that the blood urea nitrogen reduces by at least 10 mmol/L and the serum creatinine reduces by at least 100 $\mu$mol/L 24 hours after the administration. Shenkang suppository prepared according to example 1 of CN1654058 was used as positive control drug.

TABLE 4

| Administrated medicament | Daily taken times | Daily dose (mg/Kg) | Weight-average molecular weight | G/M molar ratio | Creatinine reduction after administration (μmol/L) | Blood urea nitrogen reduction after administration (mmol/L) | Effective rate (%) |
|---|---|---|---|---|---|---|---|
| Example 1 Alginic Acid Suppository | 3 | 200 | 4500 | 1.0 | 125 | 19 | 87 |
| Example 2 Alginic Acid Suppository | 1 | 300 | 3000 | 1.5 | 122 | 16 | 86 |
| Example 3 Alginic Acid Suppository | 3 | 300 | 3000 | 2.5 | 125 | 18 | 87 |
| Example 4 Alginic Acid Colon-soluble Capsule | 2 | 400 | 1500 | 1.0 | 110 | 13 | 81 |
| Example 5 Alginic Acid Suppository | 3 | 300 | 3500 | 1.4 | 121 | 15 | 85 |
| Example 6 Alginic Acid Suppository | 3 | 300 | 1800 | 2.6 | 115 | 14 | 80 |
| Example 7 Alginic Acid Suppository | 2 | 400 | 1500 | 2.8 | 118 | 14 | 82 |
| Example 8 Alginic Acid Suppository | 3 | 300 | 2000 | 5 | 121 | 15 | 84 |
| Example 9 Alginic Acid Suppository | 1 | 500 | 1000 | 10 | 119 | 13 | 81 |
| Example 10 Alginic Acid Suppository | 3 | 500 | 800 | 18 | 113 | 12 | 80 |
| Comparative Example 1 Alginic Acid Suppository | 3 | 500 | 6500 | 0.8 | 102 | 10 | 75 |
| Positive Control | 3 | 500 | — | — | 105 | 11 | 80 |

According to table 4, the suppository of the alginic acid with low molecular weight of the present invention is effective in reducing creatinine and blood urea nitrogen of patients with chronic renal failure, moreover, subject to the condition that the molecular weights were the same, the greater the G/M value is, the greater the said effects would be, and its effect corresponds to that of the positive control Shenkang suppository and is much better than that of the suppository of the alginic acid of comparative example 1.

Clinical Example 4

This clinical example explains the effects of the low molecular weight alginate salt of the present invention and the effects of the low molecular weight alginate salt of the comparative example in reducing blood glucose.

Measuring Method:

Male and female Type II diabetic subjects, without other disease or complications were selected, 48 for each sex, aged from 56 to 65 with an average age of 61, each of whom has a fasting blood glucose of more than 8 mmol/L and a blood glucose 2 hours after meal of 13.0 mmol/L. The subjects were randomly grouped, 8 subjects for each group, and orally took microcapsule of low molecular weight potassium alginate before meal 3 times per day with a daily dose of 100 to 300 mg/Kg according to Table 5, then the postprandial blood glucose before and after administration were measure. The said microcapsule of low molecular weight potassium alginate was prepared in the following way: potassium salt of alginic acid was prepared using the alginic acid with low molecular weight according to examples 1 to 10 or the alginic acid with low molecular weight according to comparative example 1, then the potassium alginate was prepared into microcapsule according to the method of example 11 or comparative example 2. The blood glucoses were measured 2 hours after meal. And Jinshi Jiang Tang Pian (0.42 g per tablet, manufactured by Long Shun Rong Pharmaceutical Factory of Tianjin Zhongxin Pharmaceutical Group Co. Ltd) was used as a positive control drug.

The results are shown in the following Table 5.

TABLE 5

| Administrated medicament | Daily dose (mg/Kg) | Weight-average molecular weight | G/M molar ratio | Postprandial blood glucose before administration (mmol/L) | Postprandial blood glucose reduction after administration (mmol/L) | Effective rate (%) |
|---|---|---|---|---|---|---|
| Example 1 Potassium Alginate Microcapsule | 300 | 4500 | 1.0 | 13.0 | 3.0 | 90 |
| Example 2 Potassium Alginate Microcapsule | 200 | 3000 | 1.5 | 13.0 | 3.0 | 92 |
| Example 3 Potassium Alginate Microcapsule | 200 | 3000 | 2.5 | 13.0 | 3.5 | 92 |
| Example 4 Potassium Alginate Microcapsule | 250 | 1500 | 1.0 | 13.0 | 3.0 | 90 |
| Example 5 Potassium Alginate Microcapsule | 300 | 3500 | 1.4 | 13.0 | 3.5 | 91 |

TABLE 5-continued

| Administrated medicament | Daily dose (mg/Kg) | Weight-average molecular weight | G/M molar ratio | Postprandial blood glucose before administration (mmol/L) | Postprandial blood glucose reduction after administration (mmol/L) | Effective rate (%) |
|---|---|---|---|---|---|---|
| Example 6 Potassium Alginate Microcapsule | 100 | 1800 | 2.6 | 13.0 | 3.5 | 92 |
| Example 7 Potassium Alginate Microcapsule | 200 | 1500 | 2.8 | 13.0 | 4.0 | 95 |
| Example 8 Potassium Alginate Microcapsule | 200 | 2000 | 5 | 13.0 | 4.2 | 95 |
| Example 9 Potassium Alginate Microcapsule | 100 | 1100 | 10 | 13.0 | 4.5 | 92 |
| Example 10 Potassium Alginate Microcapsule | 150 | 800 | 18 | 13.0 | 4.5 | 92 |
| Comparative Example 1 Potassium Alginate Microcapsule | 300 | 6500 | 0.8 | 13.0 | 2.5 | 85 |
| Positive Control | 200 | — | — | 13.0 | 2.0 | 90 |

According to table 5, the microcapsule of the low molecular weight potassium alginate of the present invention is effective in reducing postprandial blood glucose rising, moreover, subject to the condition that the molecular weights were the same, the greater the G/M value is, the greater the said effects would be, and its effect is better than that of the positive control Jinqi Jiangtang Pian and the microcapsule of the potassium alginate of comparative example 1.

Clinical Example 5

This clinical example explains the effects of the low molecular weight alginate salt of the present invention and the effects of the low molecular weight alginate salt of the comparative example in reducing calcium level in aorta vessel and improving blood rheological property.

Measuring Method:

Wister rats were sacrificed by decapitation, aortas thereof were quickly taken out and immersed in a calcium ion-free Krebs-Henseleit solution (KHS), vascular external connective tissue and intima were peeled off, and the aortas were prepared into thin sheets having a thickness of 0.5 mm. Each 20 mg vessel sheet was subpackaged in 1 ml physiological saline The subpackaged vessel sheets were added with, according to Table 6, 0.1 ml physiological saline (specific for black group), or 0.1 ml injection of alginic acid with low molecular weight sodium potassium salt (2 mmol/L), or 0.1 ml Amlodipine injection manufactured by Dalian Pfizer Co., Ltd (specific for positive control group). Said injection of the sodium potassium salt of the alginic acid with low molecular weight was prepared in the following way: sodium alginate and potassium alginate were prepared using the alginic acid with low molecular weight according to examples 1 to 10 or the alginic acid with low molecular weight according to comparative example 1, then sodium alginate and potassium alginate were prepared into an injection in a weight ratio of 17:3 according to the method of example 11 or comparative example 2. The subpackaged vessel sheets that were added with injections were incubated for 20 minutes in incubators, and then were added with calcium isotope $CaCl_2$ having a final concentration of 40 nmol/L and incubated for another 5 minutes, thereafter, were added with a stop solution pre-cooled to 5° C. and washed for 3 times, and then, were added with perchloric acid (60%) and hydrogen peroxide (30%) and digested at 80° C. for 3 hours, thereafter, Beckman LS6 500 liquid scintillation counter was used to measure radioactivity counts of calcium isotopic ion in the digestive juices, which were then converted into intake amount of the calcium isotopic ion and finally represented by calcium isotopic ion intaked by every gram of wet weight tissue (nmol).

The results are shown in the following Table 6.

TABLE 6

| Medicament administrated | weight-average molecular weight | G/M molar ratio | calcium isotopic ion intake (nmol) |
|---|---|---|---|
| Example 1 Injection | 4500 | 1.0 | 9.0 |
| Example 2 Injection | 3000 | 1.5 | 8.0 |
| Example 3 Injection | 3000 | 2.5 | 7.5 |
| Example 4 Injection | 1500 | 1.0 | 8.5 |
| Example 5 Injection | 3500 | 1.4 | 8.0 |
| Example 6 Injection | 1800 | 2.6 | 7.0 |
| Example 7 Injection | 1500 | 2.8 | 6.5 |
| Example 8 Injection | 2000 | 5 | 6.0 |
| Example 9 Injection | 1100 | 10 | 5.5 |
| Example 10 Injection | 800 | 18 | 5.5 |
| Comparative Example 1 Injection | 6500 | 0.8 | 11.0 |
| Positive Control Group | — | — | 8.0 |
| Blank Group | 0 | 0 | 14.0 |

According to table 6, the injection of the low molecular weight sodium alginate of the present invention is effective in inhibiting the intake of calcium ion, moreover, subject to the condition that the molecular weights were the same, the greater the G/M value is, the greater the said effects would be, and its effect corresponds to that of the positive control Amlodipine and is much better that that of the injection of the sodium alginate of comparative example 1. The injection of the low molecular weight sodium alginate of the present invention also serves as a calcium channel blocker. Different from Amlodipine whose blocking action takes effect quickly but too violent and lasts shortly, the low molecular weight sodium alginate of the present invention takes effect softly and its action lasts long, therefore is more suitable for use in complicated physiological environment in vivo.

Clinical Example 6

This clinical example explains the effects of the low molecular weight alginate salt of the present invention and the effects of the low molecular weight alginate salt of the comparative example in preventing increase of blood lipid when they are added into high lipid diet.

Male Wister rats weighted from 180 to 200 g were randomly divided into 13 groups, 8 for each group, wherein one group was designated as a blank group and feed with normal diet, one group was designated as a control group and feed with a high lipid diet comprising 1 wt % of cholesterol, 0.5 wt % of cholate, 10 wt % of lard oil and 10 wt % of yolk, and the remaining groups were feed with the high lipid diet and were given through stomach the potassium alginate aqueous solution according to the present invention for three times every day such that the daily intake of potassium alginate for each rat reached 6 g per day. After one month of feeding, lipoprotein in serum, total cholesterol (TC), triglyeride (TG), high density lipoprotein cholesterol (HDL-C) and low density lipoprotein cholesterol as well as very low density lipoprotein cholesterol [(LDL+VLDL)-C] were measured using enzymatic methods commonly used in the clinic (for example, CHOD-PAP to measure TC and GPO-PAP to measure TG), and the results are shown in Table 7.

said effects would be. The foresaid effect obtained by one month use of the high lipid diet containing the potassium alginate of the comparative example 1 is inferior to that obtained one month use of the high lipid diet containing the potassium alginate of the present invention, but is greater than that observed in control group which was only feed with high lipid diet.

Clinical Example 7

This clinical example explains the effects of the low molecular weight alginate salt of the present invention and the effects of the low molecular weight alginate salt of the comparative example in reducing hypertension when they are added into milk powder.

Fresh milk containing 8 wt % of solid content was added with potassium alginate until the content of the potassium alginate reached 25 wt % in term of the solid content weight, the milk was then spray dried at 150° C. to obtain a milk powder.

Male and female hypertension subjects without other disease were selected, 48 for each sex, aged from 40 to 65 with an average age of 54, whose SBP(s) were from 145 to 155 mmHg and DBP(s) were from 120 to 125 mmHg, said SBP(s) and DBP(s) were measured in resting state. The subjects were randomly grouped, 8 subjects for each group, and took the milk power after infusing it, wherein the daily dose of potassium alginate reached 10 to 30 mg/Kg and the milk power was taken continuously for one month. The blood pressure before the use of the milk power and the blood pressure after 30-day

TABLE 7

| Diet | weight-average molecular weight | G/M molar ratio | TC | TG | HDL-C | (LDL + VLPL)-C |
|---|---|---|---|---|---|---|
| Example 1 + high lipid diet | 4500 | 1.0 | 1.65 | 2.34 | 1.39 | 1.71 |
| Example 2 + high lipid diet | 3000 | 1.5 | 1.58 | 2.29 | 1.48 | 1.57 |
| Example 3 + high lipid diet | 3000 | 2.5 | 1.50 | 2.19 | 1.53 | 1.55 |
| Example 4 + high lipid diet | 1500 | 1.0 | 1.64 | 2.33 | 1.45 | 1.69 |
| Example 5 + high lipid diet | 3500 | 1.4 | 1.60 | 2.30 | 1.49 | 1.64 |
| Example 6 + high lipid diet | 1800 | 2.6 | 1.48 | 2.18 | 1.56 | 1.60 |
| Example 7 + high lipid diet | 1500 | 2.8 | 1.47 | 2.17 | 1.57 | 1.56 |
| Example 8 + high lipid diet | 2000 | 5 | 1.40 | 2.12 | 1.59 | 1.52 |
| Example 9 + high lipid diet | 1100 | 10 | 1.32 | 2.08 | 1.62 | 1.41 |
| Example 10 + high lipid diet | 800 | 18 | 1.32 | 2.08 | 1.61 | 1.42 |
| Comparative Example 1 + high lipid diet | 6500 | 0.8 | 1.80 | 2.63 | 1.31 | 2.01 |
| high lipid diet (control group) | — | — | 2.20 | 2.95 | 1.16 | 2.96 |
| Normal diet (blank group) | — | — | 0.42 | 1.10 | 2.20 | 1.02 |

According to table 7, although high lipid diet was taken, noticeable blood lipid increase preventing effect is observed after one month use of the high lipid diet containing the low molecular weight potassium alginate of the present invention, moreover, subject to the condition that the molecular weights were the same, the greater the G/M value is, the greater the use of the milk power were measured referring to the criterion of therapeutical effect made by China Hypertension League, and it was found that after one-month use of the milk power added with the potassium alginate of the present invention, the subjects' SBP(s) reduced by more than 15 mmHg and their DBP(s) reduced by more than 10 mmHg.

TABLE 8

| Milk powder taken | Weight-average molecular weight | G/M molar ratio | Daily dose (in term of potassium alginate), (mg/kg) | Average SBP/DBP before use (mmHg) | Average SBP/DBP after use for 30 days (mmHg) | Effective rate (%) |
|---|---|---|---|---|---|---|
| Example 1 milk powder | 4500 | 1.0 | 30 | 150/125 | 127/85 | 100 |
| Example 2 milk powder | 3000 | 1.5 | 30 | 148/125 | 123/87 | 100 |
| Example 3 milk powder | 3000 | 2.5 | 30 | 148/124 | 121/81 | 100 |
| Example 4 milk powder | 1500 | 1.0 | 30 | 152/125 | 120/80 | 100 |
| Example 5 milk powder | 3500 | 1.4 | 30 | 153/124 | 125/85 | 100 |
| Example 6 milk powder | 1800 | 2.6 | 20 | 150/122 | 120/80 | 100 |
| Example 7 milk powder | 1500 | 2.8 | 20 | 152/121 | 120/80 | 100 |
| Example 8 milk powder | 2000 | 5 | 15 | 151/122 | 120/80 | 100 |
| Example 9 milk powder | 1100 | 10 | 10 | 150/123 | 120/80 | 100 |
| Example 10 milk powder | 800 | 18 | 10 | 153/122 | 120/80 | 100 |
| Comparative Example 1 milk powder | 6500 | 0.8 | 30 | 151/121 | 135/90 | 87.5 |
| Common milk powder (blank group) | — | — | — | 145/125 | 145/125 | 0 |

According to table 8, noticeable blood pressure reducing effect is obtained after one month use of the milk powder containing the low molecular weight potassium alginate of the present invention, moreover, subject to the condition that the molecular weights were the same, the greater the G/M value is, the greater the said effects would be. The foresaid effect obtained by one month use of the milk powder containing the potassium alginate of the comparative example 1 is inferior to that obtained in the examples of the present invention, but is greater than that obtained in blank group which was feed with common milk powder.

The present invention can also be implemented in other various examples, those skilled in the art may make various changes or modifications according to the present invention without departing from the true scope and spirit of the invention, but such changes and modifications are within the scope of protection described in the claims of the present invention.

The invention claimed is:

1. A composition comprising an alginic acid and/or its salts with low molecular weight wherein the weight average molecular weight of said alginic acid ranges from about 800 to about 3,000 Daltons, and the molar ratio of guluronic acid units to mannuronic acid units in said alginic acid and/or its salts ranges from about 1 to about 18; and wherein the content of the alginic acid with low molecular weight and/or alginate salt ranges from about 60 wt % to about 90 wt %, or from about 30% to about 70% based on the total weight of the pharmaceutical composition; said composition may be administrated orally, rectally or parenterally for treating chronic renal failure, for improving hypertension, and for treating postprandial hyperglycemia caused by glycosidases.

2. The composition of claim 1, wherein the weight average molecular weight of said alginic acid ranges from about 800 to about 2,000 Daltons.

3. The composition of claim 2, wherein the weight average molecular weight of the alginic acid ranges from about 800 to about 1,800 Daltons, and the molar ratio of guluronic acid units to mannuronic acid units in said alginic acid ranges from about 2.6 to about 18.

4. The composition of claim 1, wherein said salt is formed from reactions of said alginic acid and a pharmaceutically acceptable cation(s).

5. The composition of claim 4, wherein the cation(s) of said salt is selected from sodium, potassium, ammonium, calcium, magnesium, zinc or combinations thereof.

6. A pharmaceutical composition useful for treating hypertension comprising the composition of claim 1 and a pharmaceutically acceptable carrier, wherein the weight average molecular weight of said alginic acid or alginate salt ranges from about 800 to about 2,500 Daltons; and the content of said alginic acid with low molecular weight and/or alginate salt ranges from about 60 wt % to about 90 wt %, or from about 30% to about 70% based on the total weight of the pharmaceutical composition.

7. The pharmaceutical composition of claim 6, wherein the pharmaceutically acceptable carrier is selected from injection class water, injection class propanediol, injection class polyethylene glycol, sodium chloride, sodium bicarbonate, sodium bisulfite, disodium edentate, potassium chloride, glucose or combinations thereof.

8. A pharmaceutical composition comprising the composition of claim 1 and a pharmaceutically acceptable carrier, wherein said pharmaceutical composition is useful for treating postprandial hyperglycemia caused by glycosidases.

9. The pharmaceutical composition of claim 8, wherein the weight average molecular weight of said alginic acid or its salts ranges from about 1,000 Daltons to about 3,000 Daltons.

10. The pharmaceutical composition of claim 8, wherein the pharmaceutically acceptable carrier is selected from starch, dextrine, calcium sulphate, calcium carbonate, calcium hydrophosphate, aluminium hydroxide, magnesium aluminum sulfate, water, ethanol, acrylic resin, polyvidone, gelatin, croscarmellose sodium, cellulose, polyethylene glycol, sodium dodecyl sulfonate, stearic acid, magnesium stearate, calcium stearate or combinations thereof; and wherein the content of said alginic acid and/or its alginate salts ranges from about 60 wt % to about 90 wt % based on the total weight of the pharmaceutical composition.

11. The pharmaceutical composition of claim 10, wherein the weight average molecular weight of said alginic acid or its salts ranges from about 1,000 Daltons to about 3,000 Daltons.

12. A pharmaceutical composition comprising an alginic acid and/or its salts with low molecular weight and a pharmaceutically acceptable carrier, wherein the weight average molecular weight of said alginic acid ranges from about 700 to about 4,500 Daltons, and wherein the content of the alginic acid with low molecular weight and/or alginate salt ranges from about 60 wt % to about 90 wt %, or from about 30% to about 70% based on the total weight of the pharmaceutical composition.

13. The pharmaceutical composition of claim 12, wherein the weight average molecular weight of said alginic acid or alginate salt ranges from about 800 to about 2,500 Daltons.

14. The pharmaceutical composition of claim 13, wherein the pharmaceutically acceptable carrier is selected from starch, dextrine, sucrose powder, lactose, glucose, calcium sulphate, calcium carbonate, calcium hydrophosphate, aluminium hydroxide, magnesium aluminum sulfate, water, ethanol, acrylic resin, polyvidone, gelatin, croscarmellose sodium, cellulose, polyethylene glycol, sodium dodecyl sulfonate, stearic acid, magnesium stearate, calcium stearate, or combinations thereof; and wherein the content of the alginic acid with low molecular weight and/or alginate salt ranges from about 60 wt % to about 90 wt %, based on the total weight of the pharmaceutical composition.

15. The pharmaceutical composition of claim 12, wherein the pharmaceutically acceptable carrier is selected from cocoa butter, fatty glyceride, polyethylene glycol, glycerogelatin, acrylic resin, polyoxyethylene monostearate, poloxamer or combinations thereof; and wherein the content of the alginic acid with low molecular weight and/or alginate salt ranges from about 30% to about 70% based on the total weight of the pharmaceutical composition.

16. The pharmaceutical composition of claim 15, wherein the weight average molecular weight of said alginic acid ranges from about 2500 Daltons to about 4500 Daltons.

17. The pharmaceutical composition of claim 12, wherein the pharmaceutically acceptable carrier is selected from starch, dextrine, sucrose powder, lactose, glucose, calcium sulphate, calcium carbonate, calcium hydrophosphate, aluminium hydroxide, magnesium aluminum sulfate, water, ethanol, acrylic resin, polyvidone, gelatin, croscarmellose sodium, cellulose, polyethylene glycol, sodium dodecyl sulfonate, stearic acid, magnesium stearate, calcium stearate, or combinations thereof.

18. The pharmaceutical composition according to claim 17, wherein the weight average molecular weight of said alginic acid ranges from about 2500 Daltons to about 4500 Daltons.

19. A method for improving hypertension comprising administering a suitable amount of the pharmaceutical composition of claim 12 to a patient.

20. A method for treating chronic renal failure comprising administering a suitable amount of the pharmaceutical composition of claim 12 to a patient.

21. A healthy food comprising an alginic acid and/or its salts with low molecular weight wherein the weight average molecular weight of said alginic acid ranges from about 700 to about 4,500 Daltons, and the molar ratio of guluronic acid units to mannuronic acid units in said alginic acid and/or its salts ranges from about 0.6 to about 19, and wherein the content of said alginic acid with low molecular weight and/or alginate salt ranges from about 60 wt % to about 90 wt %, or from about 30% to about 70% based on the total weight of the pharmaceutical composition.

* * * * *